United States Patent [19]

Franklin et al.

[11] Patent Number: 4,926,691

[45] Date of Patent: May 22, 1990

[54] APPARATUS AND METHOD FOR TESTING WOODEN POLES

[75] Inventors: Douglas E. Franklin, Abbotsford; Maurice W. Murphy; Richard A. Palylyk, both of Surrey, all of Canada

[73] Assignee: Powertech Labs, Inc., Surrey, Canada

[21] Appl. No.: 295,478

[22] Filed: Jan. 10, 1989

Related U.S. Application Data

[63] Continuation-in-part of Ser. No. 838,538, Mar. 11, 1986, abandoned.

[51] Int. Cl.$^5$ ............................................. G01N 29/04
[52] U.S. Cl. ........................................ 73/579; 364/578
[58] Field of Search .................. 73/579, 584, 12, 594, 73/602; 364/505, 506, 507, 508, 578

[56] References Cited

U.S. PATENT DOCUMENTS

| | | | |
|---|---|---|---|
| 3,043,132 | 7/1962 | Schubring | 73/579 |
| 3,877,294 | 4/1975 | Shaw | 73/579 |
| 4,059,988 | 11/1977 | Shaw | 73/579 |
| 4,297,872 | 11/1981 | Ikeda et al. | 73/579 |
| 4,399,701 | 8/1983 | Dunlop | 73/579 |
| 4,531,983 | 10/1970 | Heath et al. | 73/579 |

OTHER PUBLICATIONS

"Mechanical Vibrations" by William T. Thomson, Prentice-Hall Second Edition, Aug. 1953, pp. 174-177.
J. I. Dunlop, "Part I-Effect of Wood Degradation on Acoustic Properties of Poles" and Part II-Comparison of Non-Destructive Acoustic and Pilodyn Methods for the Detection of Decay in Posts, *Canadian Electrical Association* (Mar. 1981).
B. D. Miller et al., "A Sonic Method for Detecting Decay in Wood Poles," *American Wood-Preservers' Association* (1965).
A. J. Cserjesi, "Evaluation of the Dunlop Acoustic Scan Method of Detecting Decay Using Artificially Infected Spruce Poles," *Canadian Electrical Association* (Mar. 20, 1984).
J. E. Breeze et al., "Predicting by Sonic Measurements the Strength of Logs and Poles Having Internal Decay," *Forest Products Journal*, vol. 21, No. 5 (1969).
P. A. Cooper, "Overview and Recommendations for Wood Pole Research," *Canadian Electrical Association* (Sep. 1981).
P. Hoffmeyer, "The Pilodyn Instrument as a Non-Destructive Tester of the Shock Resistance of Wood," *Building Materials Laboratory Technical University of Denmark* (undated).
W. E. Eslyn, "Utility Pole Decay—Part I: Appraisal of a Device for Nondestructive Detection of Decay," *Wood Science and Technology*, vol. 2 (1968).
D. J. Cown, "Comparison of the Pilodyn and Torsiometer Methods for the Rapid Assessment of Wood Density in Living Trees," *Forest Research Institute, New Zealand Forest Service, Rotorua* (1978).
A. L. Shigo et al., "Detection of Discoloration and Decay in Living Trees and Utility Poles," *USDA Forest Service Research Paper NE-294* (1974).
W. C. Shortie et al., "Patterns of Resistance to a Pulsed Electric Current in Sound and Decayed Utility Poles," *Forest Products Journal*, vol. 28(1) (Jan. 1978).

(List continued on next page.)

*Primary Examiner*—John Chapman
*Assistant Examiner*—Louis M. Arana
*Attorney, Agent, or Firm*—Christie, Parker & Hale

[57] ABSTRACT

A method of determining the stiffness and condition on a wooden structure. The method consists of initiating the natural vibration of the structure in a band of frequencies that cover at least two of the first five resonant modes of vibration. An electrical response equivalent to the vibration motion of the structure is generated and the electrical response is converted to a digital signal. The resonant frequency of the structure is calculated by analysing the digital signal. By comparing the results with the results obtained using a mathematical model the stiffness and condition of the structure is determined.

9 Claims, 2 Drawing Sheets

OTHER PUBLICATIONS

A. L. Shigo, "Decay, Decayed Wood, and the Shigometer," *The International Research Group on Wood Preservation,* Document No. IRG/WP/281 (May 1980).

J. Ochrymowych, "Report of Committee P-6, Methods for Evalutation of Wood Preservatives," *American Wood-Preservers' Association,* vol. 75 (1979).

D. D. Piirto, "Critical Evaluation of the Pulsed-Current Resistance Meter for Detection of Decay in Wood," *Forest Products Journal,* vol. 28(1) (Jan. 1978).

J. D. Thornton, "Detection of Decay in Wood Using a Pulsed-Current Resistance Meter (Shigometer)," *Material und Organismen,* vols. 14(1) and 14(3) (1979).

R. D. Graham et al., "Wood Pole Maintenance Manual: Inspection and Supplemental Treatment of Douglas-Fir and Western Redcedar Poles," *Forest Research Laboratory,* (Feb. 1979).

A. H. Hearn, "Maintenance Inspection of Wood Pole Lines", *South Atlantic Wood Pole Conference,* (Apr. 1961).

W. E. Eslyn, "Utility Pole Decay, Part 3: Detection in Pine by Color Indicators," *Wood Science and Technology,* vol. 13, (1979).

R. D. Graham et al., "Controlling Biological Deterioration of Wood with Volatile Chemicals," *Electric Power Research Institute* (Aug. 1980).

W. D. Dardner et al., "Detection of Defects in Standing Poles by X-Ray Techniques," *The International Research Group on Wood Preservation* (May 1980).

C. C. Walden et al., "Sonic Examination of Marine Piles, Report on Four Years' Commercial Experience," *The Dock and Harbour Authority,* vol. 46, No. XLVI(535) (May 1965).

APPARATUS AND METHOD FOR TESTING WOODEN POLES

This application is a continuation-in-part of application Ser. No. 838,538, filed Mar. 11, 1986, now abandoned.

FIELD OF THE INVENTION

This invention relates to a nondestructive testing technique to determine the condition at or near the groundline, and the stiffness, of wooden poles, posts, marine piles and the like, particularly those buried in the ground for support.

This invention is particularly appropriate in inspecting for rot of wooden poles employed in supporting electrical conductors and telephone cables.

DESCRIPTION OF THE PRIOR ART

The requirements for reliable utility transmission and distribution systems has led to the development of many inventions to determine the amount of rot in wooden poles. Some of these inventions excite the wood fibres sonically or ultrasonically and monitor their response. Others measure electrical resistance. In general, these methods can only locate rot pockets near the monitoring probes. Other methods are influenced by outside factors such as variable moisture content of the wood, which greatly reduce their accuracy. Thus, these inventions are rarely used by utility companies.

In fact, many utility companies employ simple and subjective inspection techniques such as prodding a pole with a screwdriver or listening to the sound produced by the pole when it is struck with a hammer. Such inspection techniques are subject to extensive human error and often result in rejecting poles with superficial amounts of rot that would still be satisfactory for service.

Other utility companies reduce the subjective nature and some of the inaccuracy of these very simple inspection techniques (and thus follow a less conservative maintenance program) by x-ray or boring tests on the wood poles. These methods, however, have several disadvantages, including high cost (very high in the case of x-ray tests) and limited accuracy. Rot pockets can remain undetected if they exist outside the method's inspection zone. In the case of the boring test, the inspection zone is only a small hole in the wooden pole and for this test, there is a likelihood that rot pockets will remain undetected. Also, the portion of the pole just below the ground line, which is most subject to rotting, is very difficult to test and frequently requires extensive soil excavation prior to the test. This task greatly adds to the overall cost of the pole inspection.

Measuring pole stiffness by 3 point or cantilever bending provides useful information on the material properties of wood poles. However, this is rarely used because applying a bending movement to a service pole is usually inconvenient and costly. If the force is applied to the top of the pole the test can also be hazardous to the workers.

A review of methods and devices for wood pole testing was published by the Canadian Electrical Association (ref: 058D141). Structural dynamics testing has also been described in various publications such as the proceedings of the International Modal Analysis Conference. Prior patents known to applicants comprise U.S. Pat. Nos. 3,866,283 to Shaw; 3,664,180 to McDonald; 3,364,811 to Gnaedinger; 3,531,983 to Heath; 3,345,861 to Heath; 4,399,701 to Dunlop; 4,297,872 to Ikeda; 3,521,483 to Miller; 3,043,132 to Schubring; 4,059,988 to Shaw; 3,066,525 to Harris.

SUMMARY OF THE INVENTION

The present invention shows that the distribution of structural resonant frequencies (typically the first five modes in the infrasonic through lower sonic range- 0–100 Hz) of a pole or similar test piece is dependent on the condition of the test piece. A predictable shift in these resonant frequencies occurs as the condition of the test piece at or near the groundline is changed. The magnitudes of the resonant frequencies decrease as the condition of the test piece at or near the groundline deteriorates.

The distribution of the first five resonant frequencies of the test piece is dependent on the taper (or shape) and the general condition of the above ground portion of the test piece. The higher modes of resonance are affected to a larger degree than the lower modes of resonance due to a change in the shape or general condition of the test piece.

In accordance with the invention the test piece can be mathematically modelled and the magnitude of key model components can be determined from the distribution of the structural resonant frequencies of the test piece. The structural stiffness and the relative condition of the test piece can be accurately established based on the magnitude of the mathematical model's components as determined by the resonant frequency distribution.

The resonant frequencies of a test piece can be determined by measuring the vibration of the test piece with an attached transducer, for example an accelerometer or velocity transducer. The vibration of the test piece can be initiated by the impact of a hammer or other device. The resonant frequencies can be determined by converting the measured analog vibration signal to a digital signal and processing it through a mathematical algorithm in a digital computer. Alternatively, the analog vibration signal of the test piece can be stored on a recording and replayed, for analysis, at a later date.

This invention seeks to provide an accurate and inexpensive inspection technique and apparatus for wooden poles and the like, which overcomes difficulties and inaccuracies of previous methods.

It is another object of this invention to employ a structural resonant frequency testing method and apparatus for the nondestructive testing of wooden poles, posts, marine piles and the like capable of accounting for the effects of various test piece attachments such as crossarms, conductors and other hardware.

Still another object of this invention is to provide a structural resonant frequency testing method which is simple to perform, fast, accurate and inexpensive.

Yet another object of this invention is to provide for the detection of defects near the groundline of the pole which adversely affect the structural performance of the pole. Defects in the groundline portion of the pole will be detected whether they are at the surface or are completely hidden within the interior of the pole.

DRAWINGS

These and other aspects of the invention will be more clearly understood from a reading of the detailed description of the invention in conjunction with the drawings in which.

DESCRIPTION OF THE PREFERRED EMBODIMENTS

Figure 1:
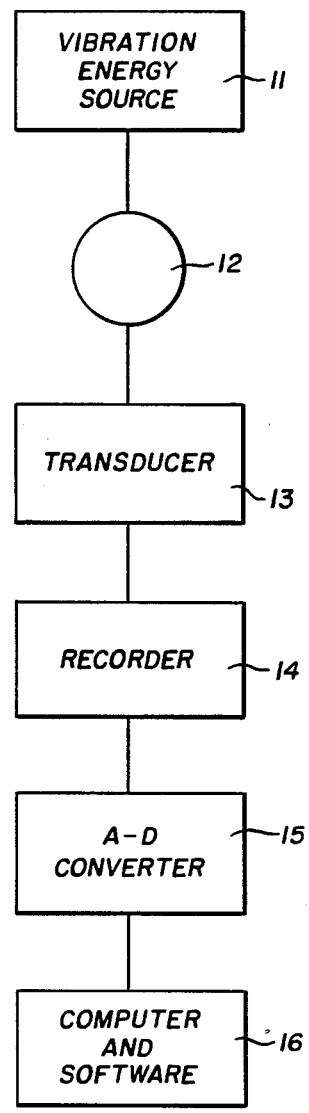
FIG. 1 is a block diagram of the method according to this invention.

FIG. 1 shows in block form, one testing method according to this invention. A vibration energy source 11 is employed to initiate the transient vibration of a test piece 12, such as a wooden pole. A transducer 13 is rigidly mounted on the same axis of the test-piece 12 as the energy source 11 and preferably located approximately six feet from the groundline. The transducer 13 is used to generate an electrical signal in accordance with the vibratory motion of the test-piece 12. A recorder 14 is used to record the transient vibration of the pole 12. At a suitable time and location, the vibration record of the pole 12 may be played back into an analog to digital converter 15, which converts the signal into a usable form. The signal is then fed into a digital computer 16 equipped with analysis software which includes an algorithm to identify the resonant frequencies from the time domain vibration trace. There are several well known algorithms of this type. The computer 16 also has a routine to determine the condition of the pole 12 based on a relationship associated with the pole's resonant frequencies. The routine to determine the condition of the pole 12 is more completely detailed in the description of FIG. 4.

In FIG. 1 the vibration source 11 may, for example, be a hammer blow.

The transducer 13 may be an accelerometer or a velocity transducer.

Figure 2:
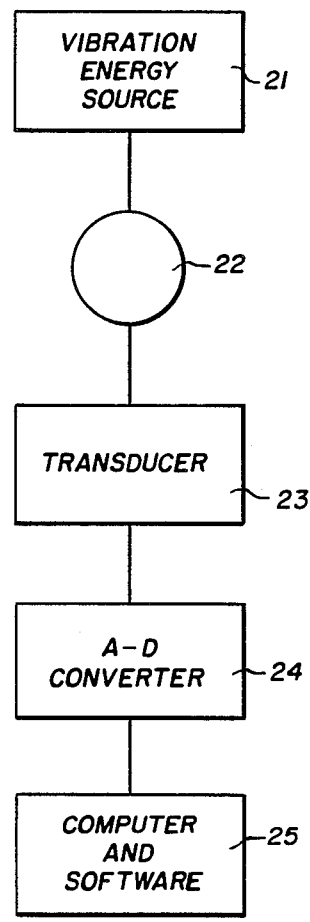
FIG. 2 is a block diagram of another embodiment of this invention.

FIG. 2 shows in block form an alternative embodiment of this invention. The electrical signal generated by a transducer 23 is directly fed into the analog to digital converter 24 bypassing the recorder 14 depicted in FIG. 1. The information is fed to digital computer 25, having the necessary software, as in computer 16. All other components of the embodiment shown in FIG. 2 allows the condition of the test piece 22 to be determined immediately following the testing procedure. In FIG. 1 the condition of the test-piece is determined at a later date at some central location.

Figure 3:
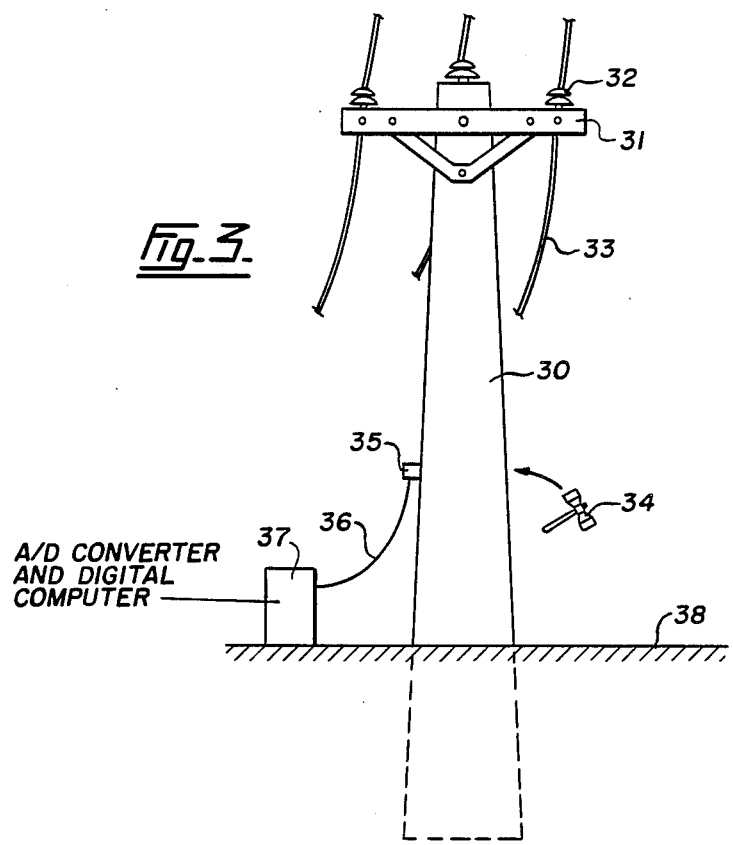
FIG. 3 is a combined pictorial and block diagram of the specific illustrative embodiment of FIG. 2.

FIG. 3 represents pictorially one illustrative embodiment of this invention and is equivalent in apparatus to the block diagram of FIG. 2. As depicted in FIG. 3, a test piece, in this case a utility pole 30, is to be tested with this invention. To perform the test, an operator makes note of the test pole 30 species, height above groundline 38, the diameter of the test pole 30 at the groundline 38 and the type, size and location on the test pole of conductors 33, crossarms 31 and insulators 32 in addition to any other significant hardware items such as transformers or guy wires. The operator then instructs the computer in the instrument 37, by means of a simple keyboard, about the test pole 30 characteristics (species, height and groundline 38 diameter) and the magnitude and location of the conductor 33 and hardware effects. Specifically, the operator would key in the location, mass, spring and damping characteristics of these components which would be known to the operator by a knowledge of each component's mass and by previous tests performed on control poles of similar conductor and hardware configurations. The operator then initiates the vibration of the test pole 30 by means of a hammer 34 of suitable size and tip hardness to excite at least two of the first five modes of vibration. The hammer impact may be at any location on the test pole 30 but is preferably about six feet up from the groundline 38 and in a direction perpendicular to the direction of the conductors 33. A transducer 35 is rigidly mounted on the opposite side of the test pole 30, on the same axis as the hammer 34 impact (at right angles to the conductor 33). Transducer 35 is preferably about six feet up from the groundline 38 and connected by means of a suitable cable 36 to the instrument 37 which contains an analog to digital converter and a digital computer. The instrument 37 processes the vibration signal and determines the resonant frequencies of the test pole 30 and, subsequently, determines the stiffness and condition of the test pole 30 by the means detailed in the description of FIG. 4.

MATHEMATICAL MODEL

Figure 4:
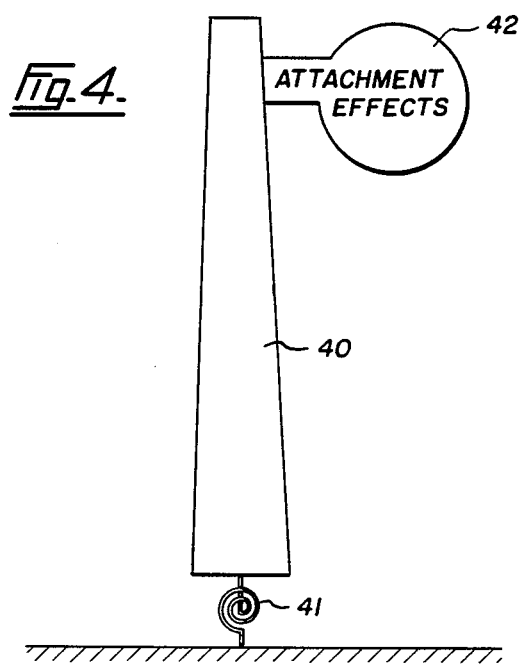
FIG. 4 illustrates the mathematical model aspects of this invention.

FIG. 4 represents, pictorially, the two dimensional model on which the mathematical formulation of this invention is based. It consists of a linearly tapered beam 40 supported by a base rotational spring 41 with some attachment effects 42 acting at some location on the linearly tapered beam 40.

The mathematical model illustrated in FIG. 4 is designed to represent a wide variety of actual pole structures, including the test pole 30 illustrated in FIG. 3. The factors which affect the natural frequencies of such an actual pole structure are the type of wood, the height, the diameter, the amount of taper of the pole, the number, size and location of attached crossarms, insulators, conductors and other attached equipment, and the amount of deterioration which has taken place near the groundline.

The mathematical model takes into account the factors which affect the natural frequencies as follows. The type of wood, the height, diameter and amount of taper is included in the formulation for the linearly tapered beam 40. The number, size and location of attached crossarms, insulators, conductors and other attached equipment is taken into account in the formulation of the attachment effects 42 in terms of their combined mass, stiffness and inertia effects on the structure. The amount of deterioration at the groundline, which is the quantity to be determined by the testing technique, is formulated by the spring constant of the base rotational spring 41.

The frequencies of the natural modes of lateral vibration for a freely vibrating linearly tapered beam are given by the following equation:

$$f(i) = \frac{[\beta^*(i)]^2}{2\pi L^2} \sqrt{\left(\frac{EI}{\rho A}\right)}$$

where
$\beta^*(i) = \beta(i)(1 - \zeta)$
and
$f(i)$ = natural frequency for each mode $i$
$L$ = length of beam
$I$ = moment of inertia for the beam
$A$ = cross sectional area of beam
$E$ = modulus of elasticity of beam
$\rho$ = density of beam
$\beta(i)$ = eigenvalue for each mode $i$ -continued ζ = amount of taper (min. diameter/max. diameter)

For a linearly tapered beam the values for I and A in the above equation apply to the maximum cross sectional dimensions of the beam.

SOLUTION OF THE MATHEMATICAL MODEL

The natural frequencies f(i) representative of an actual pole may be calculated by inserting the values pertaining to this pole into the above equation. The quantity L is taken as the measured length of the actual pole above the ground. The quantities I and A are calculated from the measured ground line dimensions of said actual pole. Knowing the wood species of the actual pole, the quantities E and η are obtained by reference to published data tables which give average values for the same type of wood species.

The remaining parameters, the eigenvalues β(i) and the taper, must be determined in order to calculate the natural frequencies. Analytical procedures for calculating eigenvalues by solving the differential equations governing free vibration of beams subject to prescribed boundary conditions are described in textbooks on vibration (for example, "Free Vibration Analysis of Beams and Shafts" by Daniel I. Gorman, published by John Wiley and Sons, the disclosure of which is incorporated herein by reference. See particularly pages 1 et seq., page 6, page 15 et seq. and page 359 et seq. at this reference). For the mathematical model illustrated in FIG. 4 the boundary conditions are the amount of taper of the linearly tapered beam 40, the location, mass, stiffness and inertia of the attachments 41, and the spring constant of the rotational spring 42.

Eigenvalue calculations may also be performed more conveniently, and for a wider range of boundary conditions, using finite element computer programs which employ, for example, the Choleski algorithm for extraction of the eigenvalues. For the finite element procedure, not less than twenty cylindrical beam elements with two degrees of freedom, rotation and translation, should be used.

Values for the location, mass, stiffness and inertia effects of the attachments 42, are normally determined experimentally, by measuring the natural frequencies of a sample pole with and without specific attachments. The effects thus determined may be applied to other poles with similar attachments. Through experiments it has been found that the stiffness effects of conductors have a negligible effect on the vibration behaviour of the pole at right angles to the conductor.

Initially, values for the amount of taper of the beam 40 and the spring constant of the base rotational spring 41 are not known. They may be determined using an iterative procedure. This is done by selecting initial approximate values for taper and spring constant. The eigenvalues β(i) and natural frequencies are then calculated for the mathematical model using the other known parameters. The resulting natural frequencies determined from the mathematical model are then compared with the measured natural frequencies of the actual pole. Taper and spring constant are then adjusted and the calculations repeated until the natural frequencies from the mathematical model closely correspond with the natural frequencies of the actual pole.

It is essential that the comparison of natural frequencies from the mathematical model and the actual pole be made with more than one natural frequency, because if only one frequency is used the iteration of taper and spring constant does not converge to a closed solution. The comparison of several natural frequencies can be conveniently performed by making use of the relationship between natural frequencies and their respective mode numbers.

It has been determined that in most cases a plot of the square root of frequency versus the respective mode number yields essentially a straight line. Such a straight line is defined by its slope and intercept at one of the axes. Thus the comparison of the natural frequencies of the actual pole and from the mathematical model can be accomplished by comparing the slopes and intercepts of the respective straight lines of the square root of frequency versus mode number plots. This comparison may be done graphically or analytically.

An exception to the straight line relationship between the square root of frequency and the respective mode number occurs when a mass is attached at a nodal point for one of the natural frequencies. The frequency for the particular mode number corresponding to this nodal point would not be on the straight line of the other frequencies. To simplify the comparison procedure under these circumstances, and any other circumstances which cause individual deviations from the straight line relationship, only the data points which follow the straight line relationship are used to make the comparison of the natural frequencies.

It has been found that the magnitude of the taper of the linearly tapered beam 40 predominantly affects the slope of said straight line, and that the spring constant of the rotational base spring 41 predominantly affects said intercept of said straight line. It has been determined that an efficient iteration procedure is to first adjust the taper until said slopes correspond, and then adjust the spring constant until said intercepts correspond.

Having determined the values for taper and spring constant for which the natural frequencies from the mathematical model closely correspond with the natural frequencies from the actual pole, the particular solution of the mathematical model is complete.

MATHEMATICAL MODEL ASSUMPTIONS

The degree to which the mathematical model truly represents the actual pole depends on the following assumptions:

a. The mathematical model assumes that the end of the beam below the base rotational spring is fixed, i.e. it assumes that resilience of the ground causes no significant effect on the natural frequencies of the actual pole. This assumption has been examined theoretically and experimentally and has been found to be valid for poles which have been installed according to standard utility procedures. For exceptional cases where poles may have been installed in excessively soft ground the solution of the mathematical model would indicate weakness in the structure due to poor soil support.

b. The mathematical model assumes that average values of the material properties E and ρ, obtained from data tables, may be used to represent the material properties of the actual pole. This assumption is valid despite the fact that the material properties of wood samples varies significantly from average values. This is because the ratio (E/ρ), used in the solution of the mathematical model, varies much less than individual values of E and ρ for a particular wood species, and the frequencies are not greatly affected by the magnitude of this ratio. According to the equation, the natural frequencies are a function of the square root of $(E/\rho)$.

c. The mathematical model assumes that the many non-uniformities in the actual pole, such as non-uniform taper, cracks, checks and knots, may be taken into account by assuming the model beam 40 to be linearly tapered.

d. It is assumed that all the detachment effects for the actual pole may be quantified for the mathematical model in terms of mass, stiffness and inertia effects. Experimental calibration may be required to initially determine these effects.

e. It is assumed that the deteriorated region of the actual pole may be represented in the mathematical model by a base rotational spring.

DETERMINATION OF GROUND LINE DETERIORATION

The amount of deterioration in the ground line region of the actual pole is determined as follows. A new solution of the mathematical model is calculated using the same input values as the previous solution except that the base rotational spring 41 is assumed to have a very high (effectively infinite) spring constant. The top deflection at a given load is calculated for both solutions by summing the deflection of the tapered beam 40 and the deflection caused by the rotational spring 41. The ratio of the top deflection using the previously calculated spring constant to the top deflection for the very high spring constant is called the relative stiffness, and this parameter can be used to assess the acceptability of the actual pole.

The top deflection for a given load using the calculated spring constant is an estimate of the static stiffness of the actual pole. The stiffness of the actual pole can be measured if a static horizontal force is applied to the top. This method has been used to confirm the validity of the nondestructive test procedure for wood poles.

The base rotational spring 41 is used to simulate rot near the groundline and an infinitely stiff base rotational spring is equivalent to the test pole having no rot. Thus, the relative stiffness is a measure of the measured stiffness versus the stiffness of the test pole 30 without preferential groundline deterioration. A test pole with a relative pole stiffness of less than 50%, for example, would indicative severe rot and the test pole would be rejected.

While we have shown and described certain illustrative embodiments of this invention, it is understood that the concepts thereof may be applied to other embodiments without departing from the spirit and scope of this invention.

We claim:

1. A method of determining the stiffness and condition of a wooden pole in the ground comprising:
   (a) initiating the natural vibration of the wooden pole in frequency band that covers at least two of the first five natural modes of vibration;
   (b) generating an electrical response equivalent to the vibration motion of the wooden pole;
   (c) converting the electrical response to a digital signal;
   (d) calculating at least two of the first five natural frequencies of the wooden pole from the digital signal;
   (e) formulating a mathematical model of the wooden pole in the ground, comprising a linearly tapered structural element connected to a spring, the linearly tapered structural element representing the portion of the pole above the ground, and the spring representing the portion of the pole below the ground;
   (f) adjusting the magnitude of linear taper and spring constant in the mathematical model until the natural frequencies of the mathematical model are substantially the same as the natural frequencies of the wooden pole;
   (g) calculating the stiffness of the mathematical model for the linear taper and spring constant thus obtained, this stiffness being equivalent to the stiffness of the wooden pole;
   (h) changing the spring constant in the mathematical model to a very large value and recalculating the stiffness of the mathematical model; a and
   (i) calculating the ratio between these two stiffnesses, called relative stiffness, which is a measure of the condition of the wooden pole near the ground line.

2. A method as claimed in claim 1 including the step of recording the electrical response equivalent to the vibration motion of the body at the site of a test for subsequent analysis.

3. A method as claimed in claim 1 in which the wooden pole is a marine pile or utility pole.

4. A method as claimed in claim 1 in which the natural vibration is initiated by a hammer blow.

5. A method as claimed in claim 1 in which the electrical response is generated by an accelerometer or velocity transducer rigidly attached to the wooden pole.

6. A method as claimed in claim 1 in which the digital signal is analyzed by a computer.

7. A method as claimed in claim 1 in which the natural vibrations of the wooden pole are initiated in the frequency range from 0 to 100 Hz.

8. A method as claimed in claim 1 in which the mathematical model is modified for the effects of conductors, crossarms and other attachments of the wooden pole using theoretical point masses, springs and the like.

9. A method of determining the stiffness of a body comprising:
   (a) initiating the natural vibration of the body in a frequency band that covers at least two of the first five resonant modes of vibration;
   (b) generating an electrical response equivalent to the vibration motion of the body;
   (c) calculating at least two of the first five natural frequencies of the body;
   (d) formulating a mathematical model of the body, comprising theoretical structural elements, point masses, springs and the like from which the natural frequencies of the mathematical model may be calculated;
   (e) adjusting at least two parameters in the mathematical model until the natural frequencies of the mathematical mode are substantially the same as the natural frequencies of the body; and
   (f) calculating the stiffness of the mathematical model for the magnitudes of at least two parameters thus obtained, for determining a stiffness equivalent to the stiffness of the body.

* * * * *